United States Patent [19]

Marrs

[11] Patent Number: 4,487,323
[45] Date of Patent: Dec. 11, 1984

[54] AUTOMATIC PARTICLE-SIZE ANALYZER
[75] Inventor: Gevan R. Marrs, Puyallup, Wash.
[73] Assignee: Weyerhaeuser Company, Tacoma, Wash.
[21] Appl. No.: 492,920
[22] Filed: May 9, 1983
[51] Int. Cl.³ .............................................. B07B 13/07
[52] U.S. Cl. .................................... 209/546; 209/408; 209/683
[58] Field of Search ....................... 209/44.3, 546, 659, 209/664, 680, 683, 287, 309, 404, 406, 407, 408

[56] References Cited

U.S. PATENT DOCUMENTS

| | | | |
|---|---|---|---|
| 3,750,884 | 8/1973 | Satake | 209/284 |
| 4,030,606 | 6/1977 | Smith et al. | 209/287 |
| 4,043,901 | 8/1977 | Gauld | 209/10 |
| 4,141,451 | 2/1979 | Lapoint | 209/664 |

Primary Examiner—Robert B. Reeves
Assistant Examiner—Donald Hajec

[57] ABSTRACT

The invention is apparatus which can automatically make a screen analysis of a granular material. The heart of the apparatus is a polygonal drum having graded screens on each of the faces except one. This open face serves as a door for introducing a sample into the interior of the drum and for discharging any material larger than the largest screen. A gear motor and crank arrangement serves to longitudinally shake the drum and agitate the sample. A second gear motor indexes the drum from screen to screen after a predetermined shaking time. Each screen fraction is accumulated on an electronic scale with weights being determined by differential weighing. The gear motors are timed by a microprocessor which also receives screen friction weight inputs and calculates a screen analysis.

8 Claims, 5 Drawing Figures

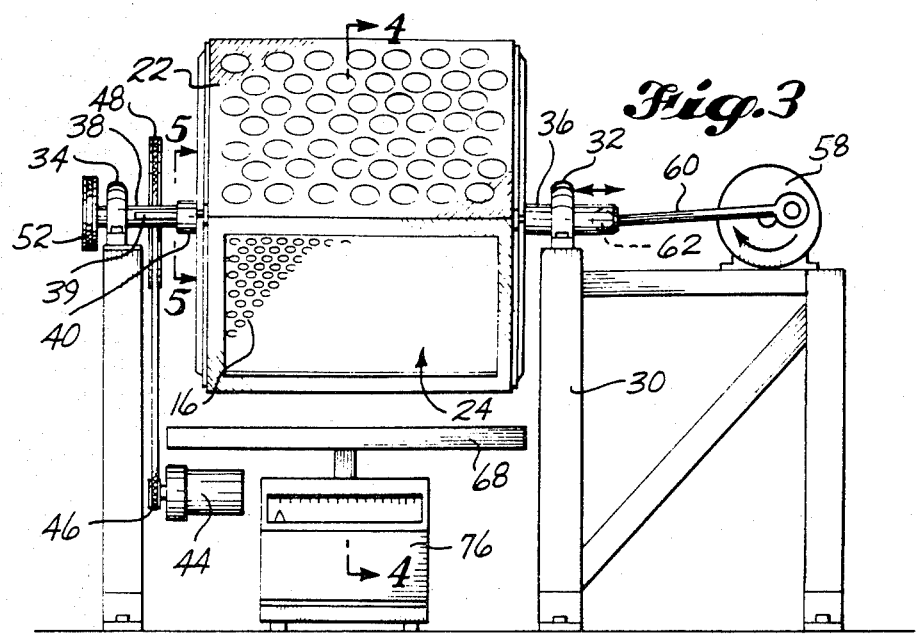
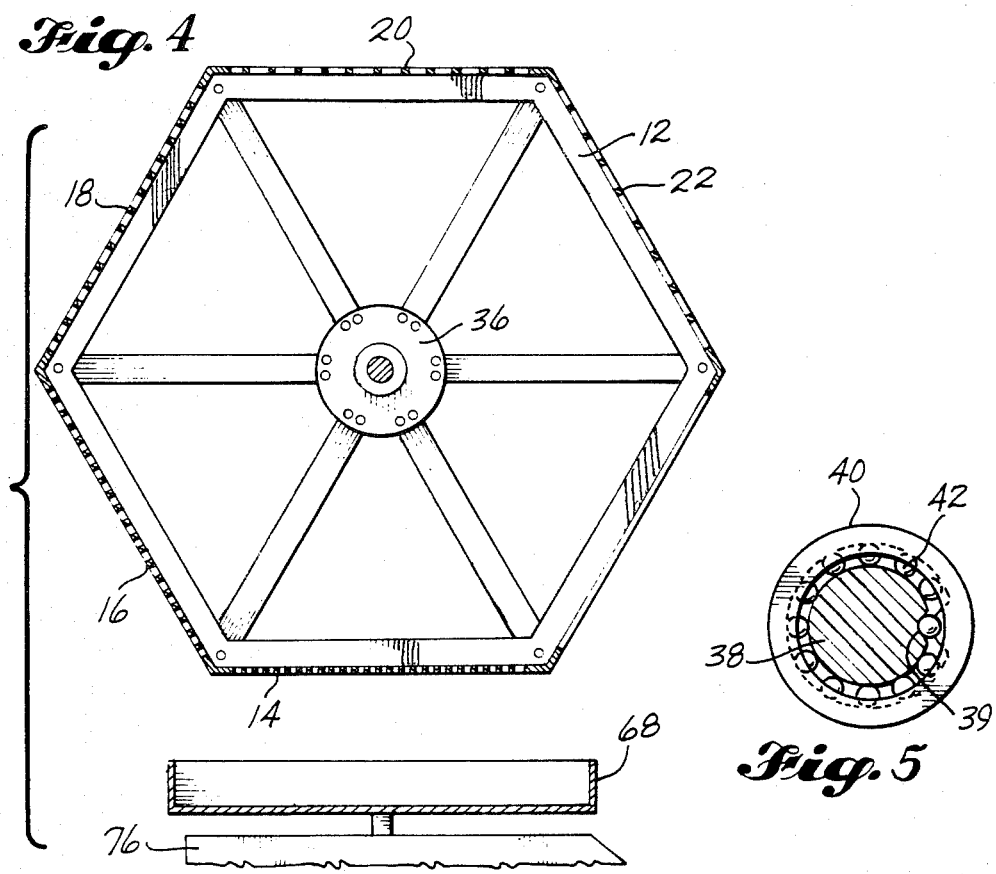

AUTOMATIC PARTICLE-SIZE ANALYZER

BACKGROUND OF THE INVENTION

The present invention is an article which can automatically make a screen analysis of a granular material. It is only necessary for an operator to introduce a sample and start the apparatus. In its preferred form, no manual weighing or calculations are necessary.

Particle-size analysis is a standard industrial test which is used on materials as varied as cereal grains, concrete aggregate, and wood chips, to draw just a few examples. Many items of commerce are sold and purchased on the basis of some predetermined size classification. Size classification data is also frequently used as input to control various manufacturing processes. This classification is usually referred to as a screen analysis, a term chosen from the laboratory method of determining the particle-size distribution. The most common method of running a screen analysis is to assemble a stack of superposed screens of graded sizes. The uppermost screen will be the coarsest and the lowermost the finest in terms of opening size. The sample to be tested is placed upon the top screen, whereupon the nest of screens is shaken for some predetermined period. After the shaking period, the material remaining on each screen and on the bottom pan is individually weighed and these weights are used to calculate a screen analysis.

A number of industrial screening processes are also based upon the concept of stacked screens of various opening sizes. In this case, the screens are usually inclined so that the fraction contained on any given screen ultimately falls from the end of the screen into a predetermined bin or onto a conveyor. Another common industrial screen is the inclined rotary drum. The surface of the drum is made of screens which may also be of sizes graded from relatively fine at the entrance end to relatively coarse at the discharge end. Once again, the various fractions are permitted to fall into separate bins or are carried away on different conveyor systems.

The development of rotary screening devices appears to have reached a mature status many years ago. Two relatively recent U.S. patents might be cited as exemplary of recent work. Satake, U.S. Pat. No. 3,750,884, shows a rice sorter which includes two polygonal drum type screens having slotted openings in a circumferential pattern. Gauld, U.S. Pat. No. 4,043,901, shows a wood chip cleaner for use on materials such as forest residual chips. This device is based on a rotary drum that separates the chips from trash and then further classifies the chips into acceptable and oversize fractions. Gauld includes a useful state-of-the-art description of rotary screens for wood chips.

In the past twenty years, the change that has taken place in the automation of laboratory testing procedures may properly be described as revolutionary. Surprisingly, this revolution has not affected screen analysis determination. This is still carried on essentially manually in the same fashion as it has been from its inception. A few new types of apparatus have been developed, but these have not been particularly useful in taking away the many manual weighing operations. U.S. Pat. No. 4,141,451 to Lapointe is such an example. This is a device for classifying wood chips by thickness. It is based upon the use of a plurality of adjustable shingled bars that form the periphery of a rotating drum. A sample is inserted into the drum which is then rotated for a given period of time with the bars set at a given spacing. The drum is then stopped, the bars readjusted to the next spacing, and rotation resumed for the prescribed time. Chips of a predetermined thickness class fall between the bars onto an oscillating inclined screen where they are further classified depending primarily upon their length or width. At the end of the test run, the individual screen fractions are collected and manually weighed.

Since the determination of screen analysis tends to be a labor intensive operation, the need has existed for a device to make such analyses on a fully automated basis. The present invention is a particle-size classifier which fills the above need. All that is necessary is to place a sample in the apparatus and start the screening operation. The end result is a printout or digital display that can give either a percentage or weight analysis of the individual screen fractions.

SUMMARY OF THE INVENTION

The present invention is a particle-size analyzer which can be fully automated to give a screen analysis without the necessity for any manual weighing steps or calculation. It comprises a polygonal drum means rotatably mounted on a longitudinal shaft or on stub shafts. The drum means has a plurality of longitudinal faces on its periphery. A plurality of screen means are mounted on the faces of the polygonal drum, one on each face, for classifying a particulate sample into size groups. The screen means are successively graded so that adjacent screens range from relatively smaller to relatively larger openings. The drum contains a door means for introducing a sample to be analyzed into the interior. An indexing means is provided for successively rotating the drum about its longitudinal axis in angular increments so that each screen in turn is located as the lowermost face of the drum. If the drum is a regular polygon, these will be increments of $(360/n)°$, where n is equal to the number of faces on the drum. There is no requirement that the drum be a regular polygon in cross section; i.e., one in which all faces are of equal edge length. In some cases it may be desirable to make the finer screens of greater area in order to achieve greater screening efficiency when the sample mass is greatest.

In order to achieve effective screening, a shaking means is coupled to the drum to give recipropcal motion along the longitudinal axis. This is a major departure from other drum classifiers which rotate in order to tumble a sample to provide agitation. The indexing means and the shaking means are coupled to a control means which determines the shaking time for each screen. After this time has elapsed, the control means directs the shaking means to stop and the indexing means to rotate the drum to the next larger screen size. A new period of shaking then ensues, after which the drum is again indexed to the next larger screen size. Ultimately, the last of the sample is removed from the drum. This may be done either through a final screen having openings sufficiently large to pass the remainder of the sample or, preferably, from an open face of the drum on which no screen means was mounted. Under the drum, a means is provided for collecting and weighing successive screen fractions of the sample being analyzed.

In the most preferred form of the invention, the control means is a microprocessor which will have programmed into it the necessary information on shaking times and will signal the indexing means when it should advance to the next angular increment. In this most preferred form of the invention, the particle-size analyzer will also include a scale associated with the collecting means. The scale may also be integrated with the microprocessor so that the microprocessor will receive inputs of the weights of each successive screen fraction. These can readily be calculated by difference. From the knowledge of the weight of each screen fraction and the total accumulated weight at the end of the screening run, the microprocessor can then calculate a percentage screen analysis. This can be displayed in many ways. In most cases, the most convenient display will be a printout of the screen analysis. The results can also be displayed digitally or can be directed to some more remote location such as to a process control computer.

It is thus an object of the present invention to provide a fully automatic particle-size analyzer.

It is another object to provide a particle-size analyzer which does not require manual weighing or calculation in order to determine a screen analysis.

It is a further object to provide an automatic particle-size analyzer which is dependable in operation and relatively simple in mechanical construction.

These and many other objects will become readily apparent to those skilled in the art upon reading the following detailed description taken in conjunction with the drawings.

BRIEF DESCRIPTION OF THE DRAWINGS

FIG. 3 is a front elevation view.

FIG. 4 is a side elevation shown as a section through line 4—4 of FIG. 3.

FIG. 5 is a side elevation in section showing detail along line 5—5 of FIG. 3.

DETAILED DESCRIPTION OF THE PREFERRED EMBODIMENTS

Figure 1:
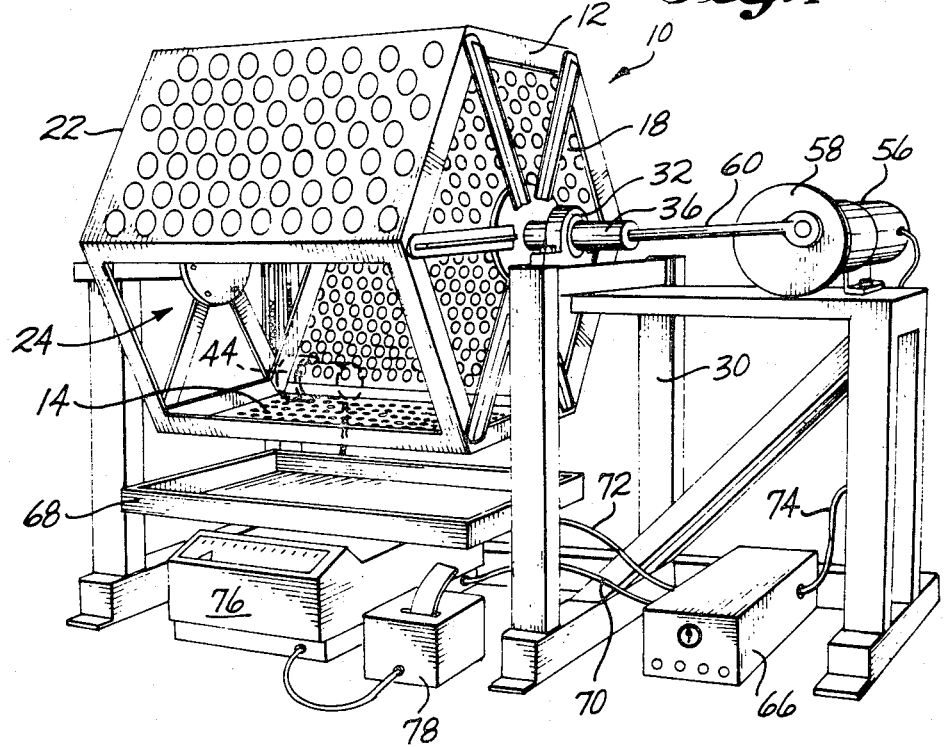
FIG. 1 is a perspective representation of the particle-size analyzer taken in front elevation from a viewpoint slightly to one side.
Figure 2:
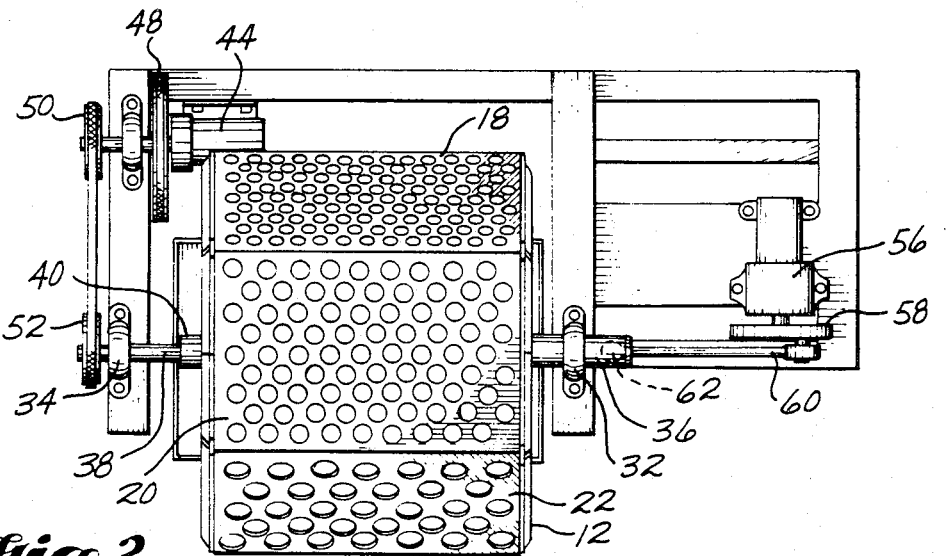
FIG. 2 is a top plan view of the analyzer.

The construction and operation of the automatic particle-size analyzer will now be described in detail. Referring to the figures, the heart of the device is a polygonal drum generally shown at 10. This consists of a structural frame 12 made of angle iron or other suitable structural material. In the embodiments shown, the ends of the drum are of spoke construction. Alternatively, these ends could be formed as a solid wall. In the representation shown, the drum has a hexagonal cross section with six longitudinally oriented faces. Five of these faces are covered with screens 14, 16, 18, 20, and 22 of which screen 22 has the largest openings and screen 14 the smallest. The screens are arranged so that the opening size is graded with each adjacent screen having relatively larger openings than the screen preceding it. The sixth face of the drum 24 is left as an open side. This serves as a convenient door through which the sample is initially introduced into the drum onto screen 14 and through which the largest oversized particles can be discharged at the end of the screening cycle.

As will be understood by those skilled in the art, the term "screen" should be broadly construed. While the examples shown in the drawings are perforated plates, they could also be woven wire screens, parallel bar screens, or other size grading devices of known construction or geometric configuration.

The polygonal drum and its associated drive equipment are mounted on a frame 30. Pillow blocks 32 and 34 are bolted to the frame and support the drum on shafts 36 and 38. Shaft 38 is an extension mounted telescopically in shaft 40 which is the shaft member actually affixed to the drum. The purpose of this arrangement will be explained later in the description. A drive motor 44, which is conveniently a high ratio gear reduction motor, serves as the indexing device to rotate the drum so that successive screens are in the down position. Motor 44 is coupled to the drum through a further speed reducing means consisting of belts and sheaves 46, 48, 50 and 52.

One of the unique features of the present invention is that it combines the best features of a drum type classifier and shaking screen. In this regard, another gear motor 56 serves to impart a reciprocating shaking action to the entire polygonal drum. This is accomplished by a crank 58 which is coupled to the drum through a rod 60 bearing a ball end 62 retained within the outboard end of shaft 36. As the reciprocating motion is imparted to the drum through this crank arrangement, shaft 36 will slide back and forth in pillow block 32. At the opposite end of the drum, shaft 38 is permanently fixed within pillow block 34 so that it does not oscillate back and forth. If this was to occur, a much more complex drive system for indexing the drum from screen to screen would be required. To accommodate the reciprocating motion, shaft 38 moves telescopically within shaft 40. This is conveniently accomplished by the use of a linear Ball Bushing having recirculating balls 40 (FIG. 5). One of the balls rides in a shaft detent 39 so that rotary motion can be transmitted to the drum by motor 44 and its associated drive system. In the preferred form of construction, shaft 38 would be held within shaft 40 by two such bushings or some similar bearing arrangement in order to prevent angular deflection from occurring between the drum and shaft 38.

In operation, a sample would be placed on screen 14 with the drum oriented as shown in FIG. 1. An operator would then trip the appropriate switch on control box 66 which contains a microprocessor and associated electrical cables 72, 74 to the two drive motors and cable 70 to the scale at the particle-receiving section. With the sample being tested resting on screen 14, the polygonal drum would reciprocate for a predetermined length of time so that the material finer than the openings in screen 14 would pass through and be retained on receiving tray 68. The receiving tray rests on an electronic scale 76, which is tied through electrical control cable 70 to the control box 66. Scale 76 is also in electrical communication with a printer 78, said printer also being interconnected electrically with the microprocessor in control box 66.

Depending both on the nature of the material being screened and on the size of the opening in the screen, it will be the usual practice to have longer shaking times when the samples are on the smaller screens. This is because more sample is present and more agitation is required to ensure that all portions of the sample are exposed to the screen surface.

As one example of a screen constructed according to the teachings of the present invention, the polygonal drum was constructed as a hexagon in cross section. The faces accommodated screens 42 cm wide and 65 cm long. The crank wheel was driven at 155 rpm and had a crank offset of approximately 45 mm so that the drum was reciprocated a total of 90 mm during each stroke. The drum was indexed from screen to screen by a magnetic brake-equipped motor having a 13.5 rpm output speed. This speed was further reduced by a factor of about 10 through the belt and pulley system. The programmable controller was programmed so that the drive motor 44 produced a clockwise rotation in the drum of 60 degrees following each shaking period.

Using the system described, it is not necessary to begin with a sample of known weight. All of the material charged to the polygonal drum will ultimately be recovered on pan 68. The increments which comprise each screen fashion can be summed to equal the original starting weight. The amount of screened material which comprises each screen fraction is determined by difference just prior to the time the programmable controller signals motor 44 to rotate the drum to the next larger screen size.

While the preceding description includes the best mode known to the inventor of practicing the present invention, it will be evident to those skilled in the art that many departures can be made from the specific construction and method of operation taught in the present disclosure. As one example, it is not absolutely essential that one face of the drum be left completely open. It is equally within the scope of the invention to admit the sample into the drum through a door which could be located in one of the end walls. Further, it is not absolutely essential that the collecting means include a scale which is integrated with the microprocessor. Thus, the scope of the invention should be considered to be limited only in accordance with the following claims.

What is claimed is:

1. A particle-size analyzer which comprises:
   a. a polygonal drum means having a plurality of longitudinal faces on the periphery of said means;
   b. a plurality of screen means mounted on the faces of the drum means for classifying a particulate sample into size groups, said screen means being successively graded from relatively smaller to relatively larger openings;
   c. a door means for introducing a sample to be analyzed into the interior of the drum;
   d. indexing means for successively rotating the drum about its longitudinal axis in angular increments so that each screen in turn is located as the lowermost face of the drum;
   e. shaking means giving reciprocal motion along the longitudinal axis of the drum in order to agitate a sample being analyzed;
   f. control means which determines shaking time for each screen means and directs the indexing means to rotate the drum to a next larger screen size after a predetermined period of shaking, and
   g. means for collecting successive screen fractions of the sample being analyzed.

2. The particle-size analyzer of claim 1 in which the control means is a microprocessor.

3. The particle-size analyzer of claim 2 in which the collecting means includes a scale integrated with the microprocessor so that the microprocessor receives inputs of the weights of each successive screen fraction and calculates a percentage screen analysis.

4. The particle-size analyzer of claim 1 in which the door means is an open face on the drum means.

5. The particle-size analyzer of claim 4 in which the open face is adjacent to the screen having the smallest openings.

6. The particle-size analyzer of claim 1 in which the door means is located in one end of the drum.

7. The particle-size analyzer of claim 1 in which the drum is a regular polygon in cross section.

8. The particle-size analyzer of claim 7 in which the indexing means rotates the drum in angular increments of $(360/n)°$, where n is equal to the number of faces on the drum.

* * * * *

UNITED STATES PATENT AND TRADEMARK OFFICE
CERTIFICATE OF CORRECTION

PATENT NO. : 4,487,323

DATED : December 11, 1984

INVENTOR(S) : Gevan R. Marrs

It is certified that error appears in the above—identified patent and that said Letters Patent is hereby corrected as shown below:

In the Abstract, the penultimate line, the word "friction" should read -- fraction --.

Signed and Sealed this

Twenty-first Day of May 1985

[SEAL]

Attest:

DONALD J. QUIGG

*Attesting Officer*  *Acting Commissioner of Patents and Trademarks*